United States Patent [19]

Collazo

[11] Patent Number: 5,326,368
[45] Date of Patent: Jul. 5, 1994

[54] MODULAR ACETABULAR CUP

[75] Inventor: Carlos E. Collazo, Ridgefield Park, N.J.

[73] Assignee: Howmedica, Inc., New York, N.Y.

[21] Appl. No.: 950,089

[22] Filed: Sep. 22, 1992

[51] Int. Cl.⁵ .................................................. A61F 2/34
[52] U.S. Cl. ........................................ 623/22; 623/18
[58] Field of Search .................. 623/16, 18, 20, 22, 623/23

[56] References Cited

U.S. PATENT DOCUMENTS

| | | | |
|---|---|---|---|
| 4,324,006 | 4/1982 | Charnley | 623/22 |
| 4,563,778 | 1/1986 | Roche et al. | 623/22 |
| 4,566,138 | 1/1986 | Lewis et al. | 623/22 |
| 4,596,580 | 6/1986 | Weill | 623/22 |
| 4,676,798 | 6/1987 | Noiles | 623/22 |
| 4,883,488 | 11/1989 | Bloebaum et al. | 623/20 |
| 4,944,757 | 7/1990 | Martinez et al. | 623/10 |
| 4,955,325 | 9/1990 | Zarnowski et al. | 623/22 |
| 5,074,881 | 12/1991 | Thull et al. | 623/22 |
| 5,108,447 | 4/1992 | Zeiler et al. | 623/22 |
| 5,176,771 | 1/1993 | Grimes | 623/22 |
| 5,192,329 | 3/1993 | Christie et al. | 623/22 |

FOREIGN PATENT DOCUMENTS

| | | | |
|---|---|---|---|
| 0303006 | 2/1988 | European Pat. Off. | 623/22 |
| WO92/15261 | 9/1992 | PCT Int'l Appl. | 623/22 |

Primary Examiner—David Isabella
Attorney, Agent, or Firm—Pennie & Edmonds

[57] ABSTRACT

A modular prosthetic acetabular cup for use in restorative hip replacement is disclosed. The acetabular cup is of modular construction whereby extension members can be attached to an acetabular cup to provide a acetabular cup device with a cross section of a desired configuration. The extension members can be attached to the acetabular cup by means including dovetail joints, mechanical fasteners, and locking taper joints similar to those in femoral hip components.

15 Claims, 5 Drawing Sheets

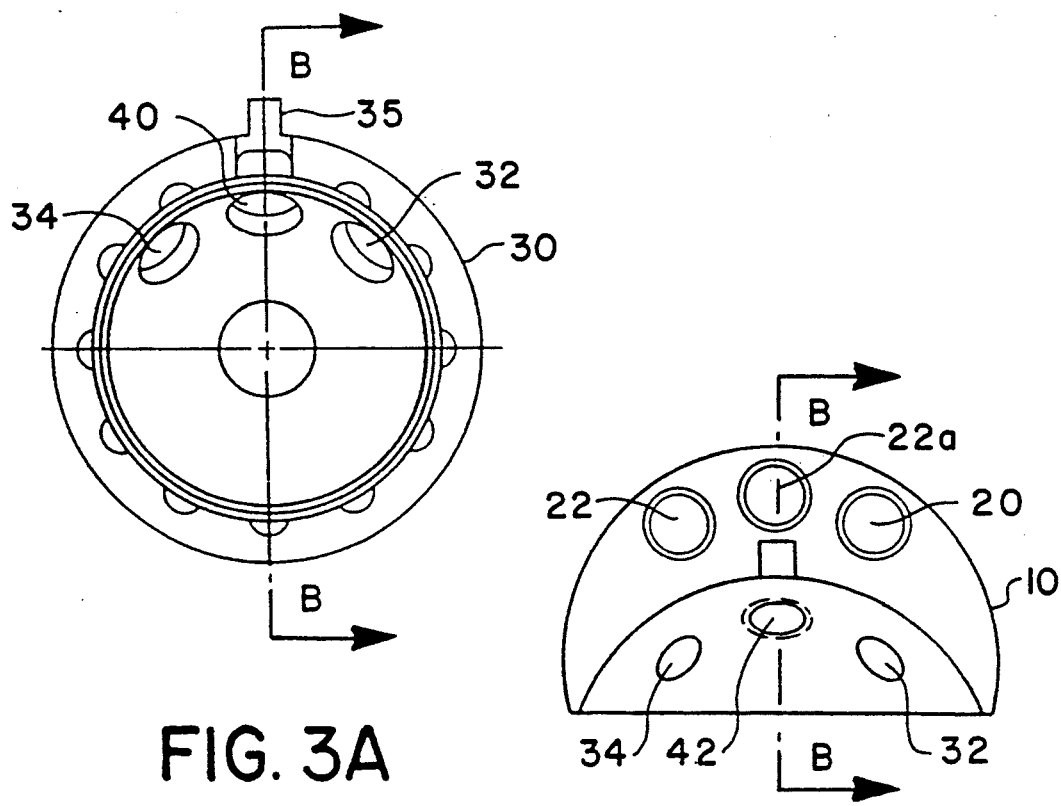
FIG. 3A
FIG. 3B
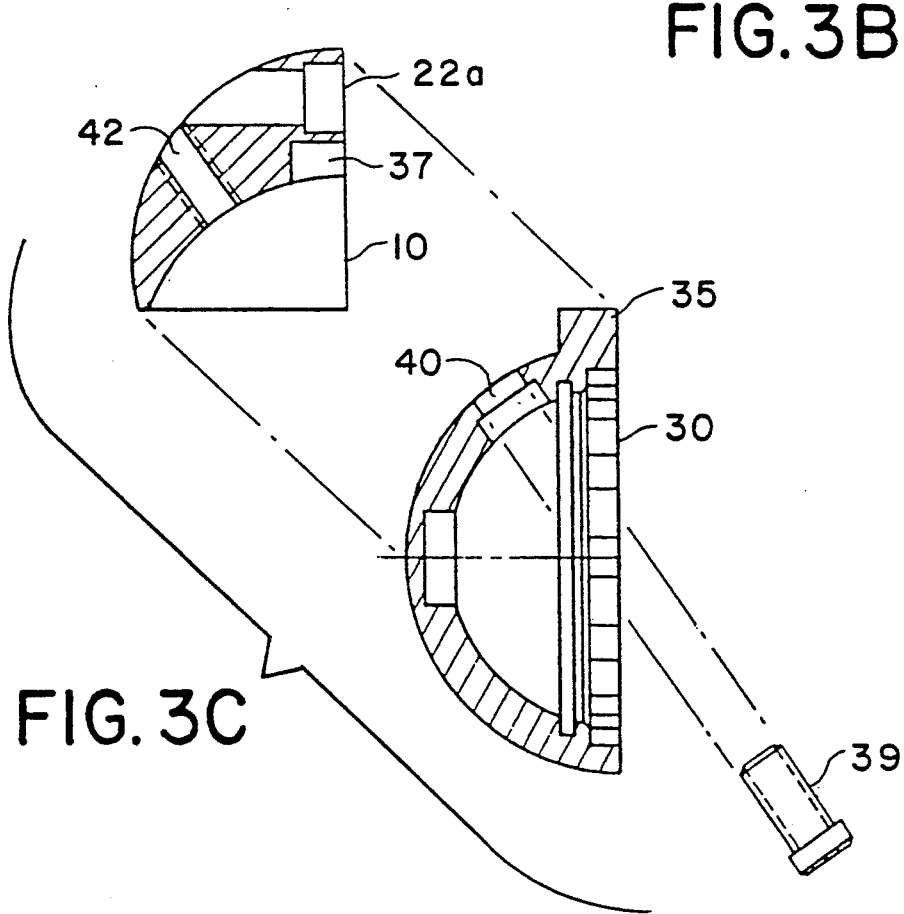
FIG. 3C

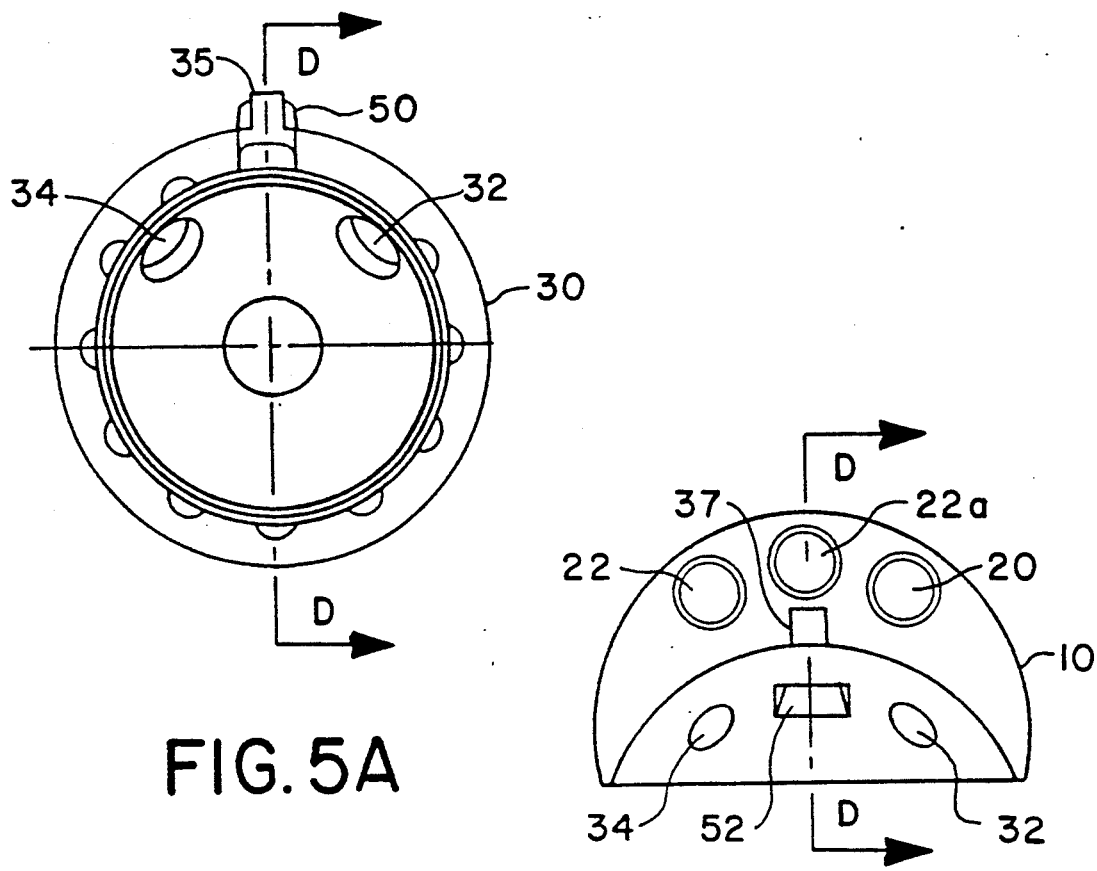
FIG. 5A
FIG. 5B
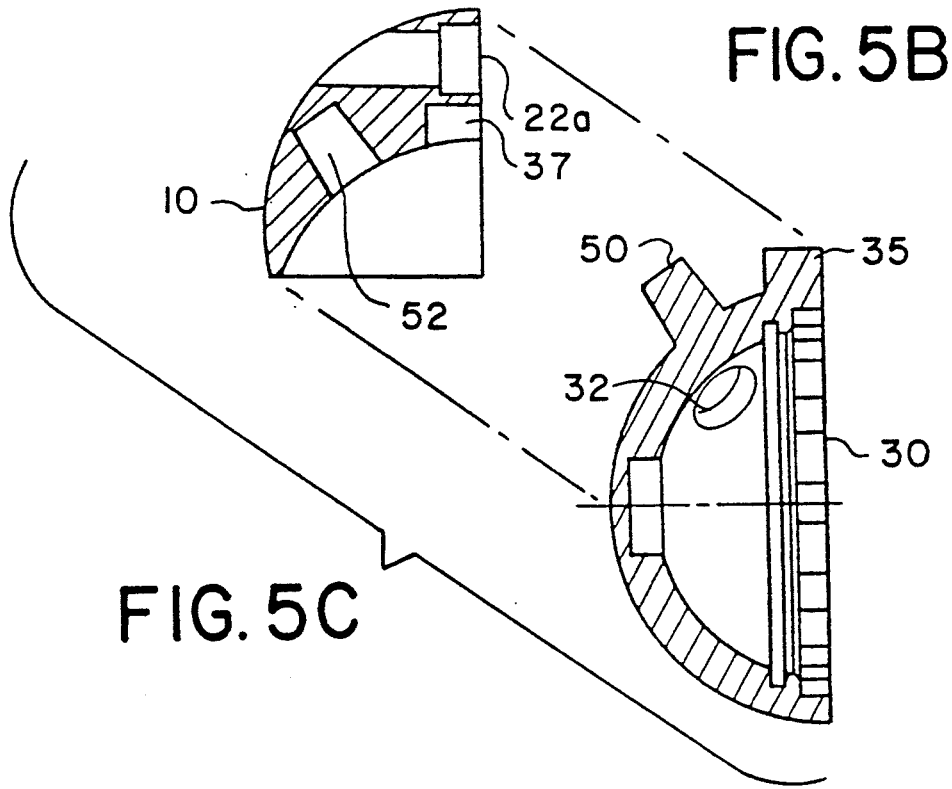
FIG. 5C 5,326,368

MODULAR ACETABULAR CUP

FIELD OF THE INVENTION

This invention relates to artificial joint implants. More particularly, this invention relates to modular, multi-component acetabular cup joint implants.

BACKGROUND OF THE INVENTION

Many different types of prosthetic hip implants are known in the art. For example, prosthetic hip joint implants such as those found in U.S. Pat. No. 4,596,580 and U.S. Pat. No. 4,955,325 which employ acetabular cups are typical of prior art devices. However, these implant devices tend to be deficient where the primary acetabular cup has migrated superiorly to produce an oval acetabulum in the pelvic bone. In those circumstances, the surgeon typically must fill the superior portion of the acetabulum with bone grafts, ream a hemispherical cavity, and insert a new acetabular cup component. This is both time consuming, expensive and exposes the patient to risk. Further, when the acetabulum is oval in shape, it is difficult to achieve an intimate interface between the bone and the implant without use of allografts which are difficult to obtain and which present potential health risks due to spread of infectious diseases.

Oval shaped acetabular cups are known in the art. See EP 303,006. These cups, however, are provided only in a fixed configuration and cannot be altered to fit oddly shaped cavities that might be discovered during surgery.

A need therefore exists for an acetabular cup implant for use in hip restoration that provides an intimate interface between the bone and the implant and which can readily be adapted to fill oval acetabulums without the attendant disadvantages of the prior art devices.

SUMMARY OF THE INVENTION

In accordance with the invention, a modular acetabular cup device for use in restorative hip replacement is provided. The present invention includes an extension member adapted to engage an acetabular cup to provide a modular acetabular cup device that substantially conforms to the shape of the existing cavity in the pelvis and provides a cross section of a desired configuration. The extension member includes an open hollow interior portion that terminates in a base section. The acetabular cup has an outer surface that includes locking means to engage the extension member to substantially prevent relative movement between the acetabular cup and the extension member. Such locking means may include extending ribs, anti-rotation keys, dove-tail joints, mechanical fasteners or taper members.

The outer surface of the extension member can be spherical or oval shaped to enable the device of the invention to substantially conform to cavities of various configurations. The outer surface of the extension member can be at least partially, oval in cross section and extend up to about 90 degrees to a polar axis through the center of the extension member through an arc about 180 degrees. Optionally, a layer of bone cement may be provided between the acetabular cup and the extension member.

The modular acetabular cup device of the invention conveniently may be provided in the form of a kit that at least includes an extension member and an acetabular cup. The kit may further include an assortment of extension members, a wrenching tool, mechanical fasteners, bone cement layers and a sterile container for holding the various components.

BRIEF DESCRIPTION OF THE DRAWINGS

FIG. 3A is a bottom plan view illustrating an alternative embodiment of an acetabular cup component including an anti-rotation key;

FIG. 3B is a bottom plan view illustrating an extension member including an anti-rotation key;

FIG. 3C is an exploded cross sectional view along lines B—B of an assembled modular acetabular cup including an anti-rotation key;

FIG. 5A is a bottom plan view illustrating an alternative acetabular cup component including an anti-rotation key and a taper lock in accordance with another alternative embodiment of the present invention;

FIG. 5B is a bottom plan view illustrating an extension member including an anti-rotation key and a taper lock; and FIG. 5C is an exploded cross sectional view along lines D—D, illustrating an assembled modular acetabular cup including an anti-rotation key and a taper lock.

DETAILED DESCRIPTION OF THE INVENTION

Figure 1A:
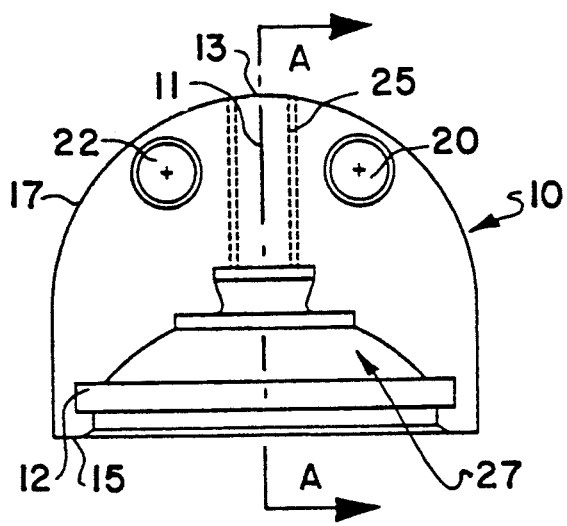
FIGS. 1A–1C are side views illustrating different embodiments of extension members for use in the modular acetabular cups of the invention.
Figure 1D:
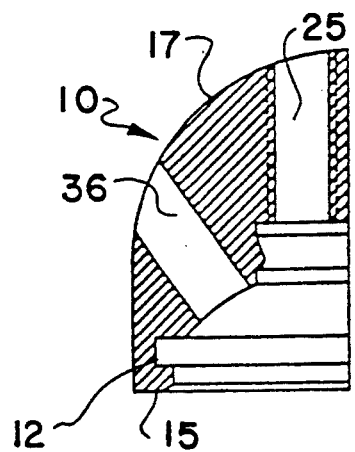
FIGS. 1D–1F are cross-sectional views of the extension members of FIGS. 1A–1C, respectively, along lines A—A.
Figure 1B:
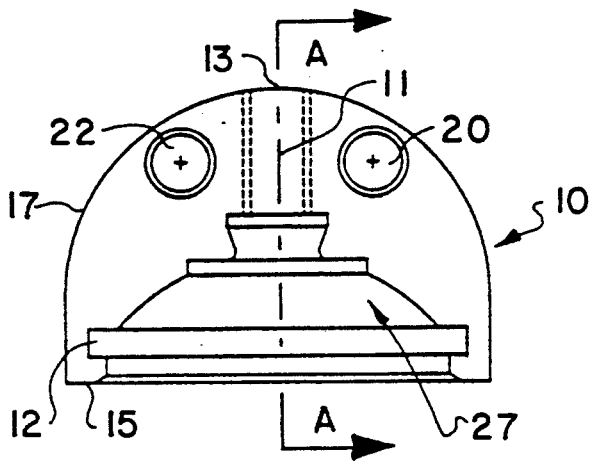
Figure 1E:
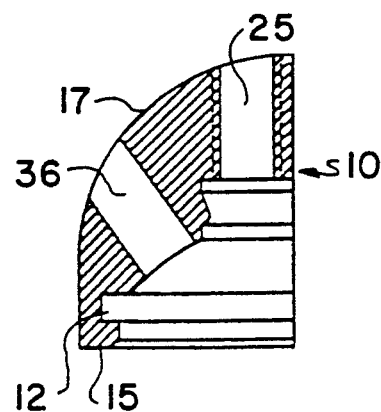
Figure 1C:
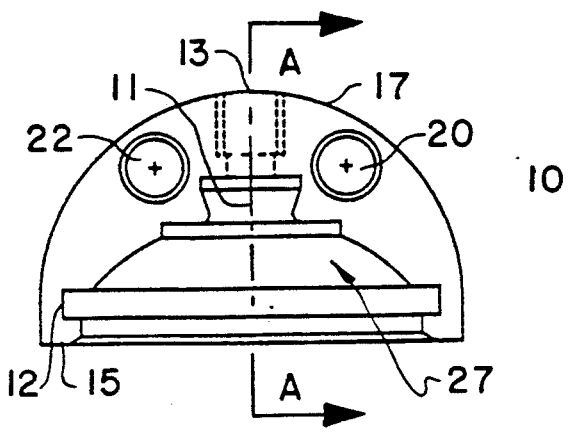
Figure 1F:
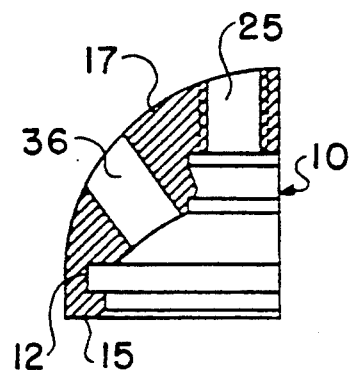

As shown in FIGS. 1A–1C, extension member 10 generally has a half-rounded shaped cross-section. However, as also shown in FIGS. 1A–1C, the cross-section of extension member 10 can be varied from the substantially half-oval cross section shown in FIGS. 1A and 1D to the substantially hemispherical cross-section shown in FIGS. 1C and 1F. It will be appreciated by persons skilled in the art that virtually any shape outer surface can be provided as required.

As shown in FIGS. 1A–1C, extension member 10 has an axis 11 extending between base 15 and apex 13. The circumferential surface 17 of extension member 10 that contacts a bone surface, such as the pelvis (not shown) tapers inwardly in the direction from base 15 to apex 13. The outer surface of the extension member may extend up to 90 degrees to axis 11 through an arc of 180 degrees to define an elliptical or otherwise rounded configuration. Holes 20 and 22 are provided in extension member 10 on opposite sides of threaded bore 25. Holes 20 and 22 can be positioned perpendicular to or at another angle relative to bore 25 to receive bone screws (not shown) to anchor the assembled modular acetabular cup to a bone member.

Figure 2A:
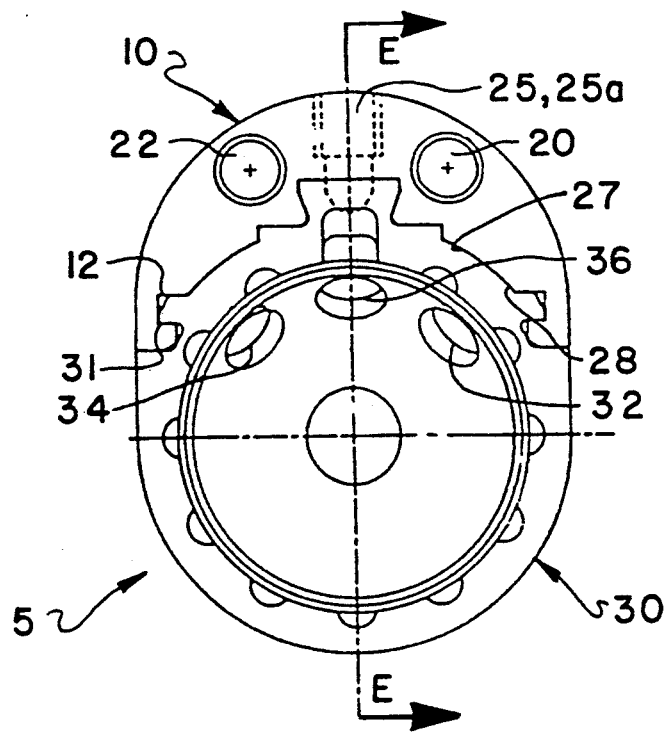
FIG. 2A is a bottom plan view illustrating an assembled modular acetabular cup including a laterally extending rib for engaging an extension member in accordance with the invention.
Figure 2B:
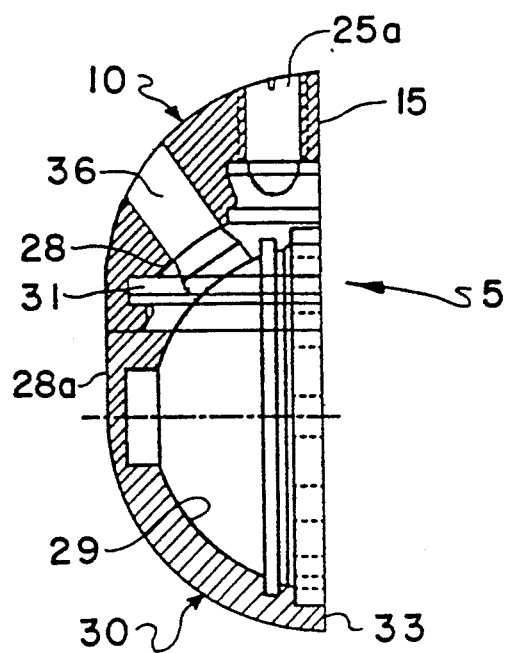
FIG. 2B is a cross-section view along line E—E of FIG. 2A.

As shown in FIGS. 2A–2B, extension member 10 has interior surfaces 27 that match the exterior surface 28 of acetabular cup component 30 to provide an intimate fit between those components to form the modular acetabular cup device 5 of the invention. A second portion 28a of the exterior surface is adapted to engage the bone. Acetabular cup component 30 generally is in the form of a hollow, hemispherical cup that has a base 33 and a spherical, inner surface 29. When assembled, base 15 and base 33 lie in substantially the same plane. In an embodiment of the invention shown in FIGS. 1A–1F and FIGS. 2A–2B, radial groove 12 can be provided in the interior surface of extension member 10 to engage extending lateral rib 31 of cup component 30 to substantially prevent relative movement between extension member 10 and cup component 30. Extension member 10 and cup component 30 are secured against relative movement by locating locking set screw 25a in bore 25 as shown in FIG. 2B.

Upon securing extension member 10 and cup component 30 against relative movement, the assembled modular acetabular cup 5 can be anchored in a cavity in a bone member. Anchoring of modular acetabular cup 5, as shown in FIG. 2B, can be achieved by locating bone screws (not shown) through holes 20 and 22 in extension member 10 as previously discussed or through holes 32, 34 or 36, which penetrate both the cup and extension member. Other than the holes for the bone screws, the cup and extension member together preferably form a substantially continuous outer surface for engaging the pelvis.

In an alternative embodiment of modular device 5 as shown in FIGS. 3A–3C, acetabular cup component 30 is provided with anti-rotation key 35. Anti-rotation key 35 mates with recess 37 in extension member 10 to substantially secure these components against relative movement. Anti-rotation key 35 also absorbs torsional loads placed on modular acetabular cup 5 after implantation into an acetabulum.

As shown in FIG. 3C, cup component 30 and extension member 10 are secured together by locking screw 39 placed through hole 40 in the cup and threaded hole 42 in the extension member. Bone screws (not shown) can be passed through holes 22, 22a and 20 in extension member 10 and or through holes 32 and 34 to secure the modular device to the bone.

Figure 4:
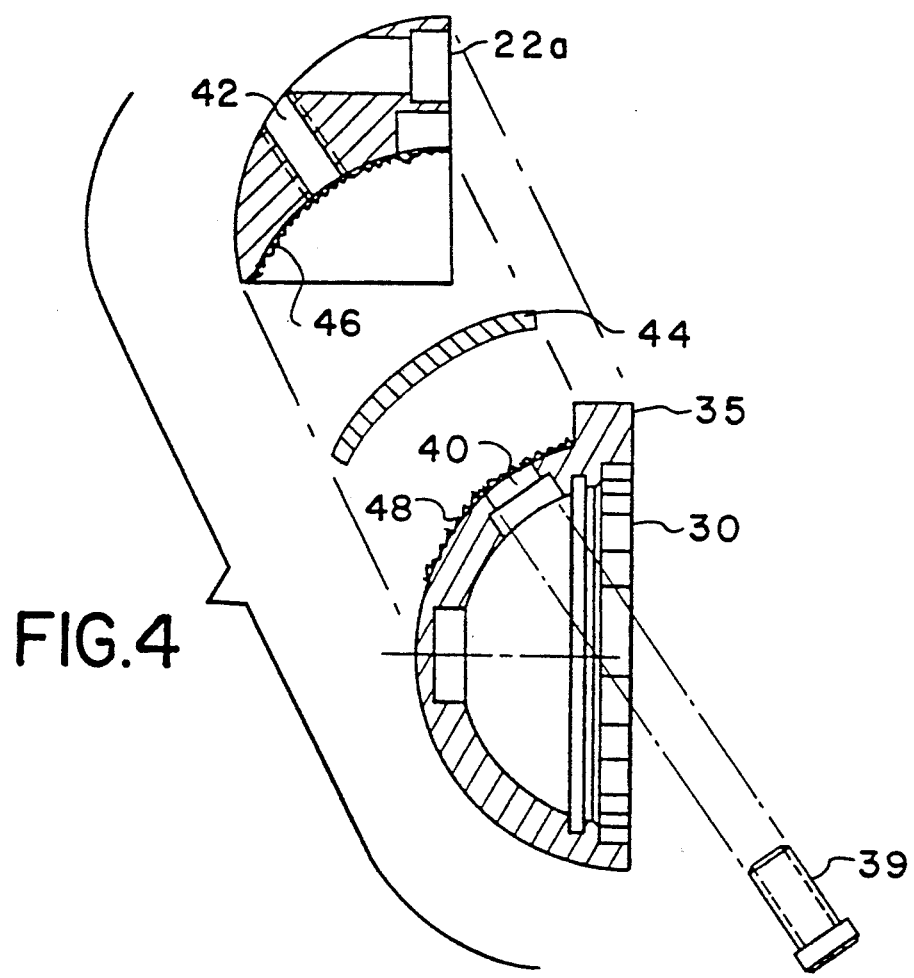
FIG. 4 is an exploded cross sectional view along lines B—B, illustrating a further alternative embodiment of an assembled modular acetabular cup including an anti-rotation key and an intermediate layer of bone cement.

In yet another embodiment of the modular acetabular cup of the invention, as shown in FIG. 4, a layer of bone cement 44 can be placed between acetabular cup component 30 and extension member 10. Generally, the mating surfaces of extension member 10 and cup component 30 are machined to provide a mechanical interlock for the cement as shown at 46 and 48 to assist in retaining bone cement layer 44 prior to joining the cup and extension member with mechanical fasteners such as screw 39. The embodiment of FIG. 4 is otherwise similar to that shown in FIGS. 3A–C.

In a still further embodiment of the modular acetabular cup 5 of the invention, and as shown in FIGS. 5A–5C, acetabular cup component 30 is provided with a locking taper member 50 to mate with a corresponding recess 52 in extension member 10. Anti-rotation key 35, as previously discussed, also may be included on cup component 30 to further secure the components and resist torsional loads. Further locking of the cup component and extension member can be achieved by a locking screw as shown in FIGS. 4 and 3C. The assembled device is secured to the bone member by bone screws through any of holes 22a, 20, 32, 22 and 34.

Although each of the aforedescribed embodiments of the modular acetabular cup of the invention may be employed independently, it is to be noted that the embodiments shown in FIGS. 1-5 can be employed in combination. Accordingly, acetabular cup component 30 may be provided with various combinations of anti-rotation keys, radial grooves, taper members and the like. Both cup component 30 and extension member 10 also may include additional stabilizers such as spikes, fins or pegs. Both cup component 30 and extension member 10 further may include bone ingrowth/outgrowth surfaces, such as sintered beads, cast mesh, or plasma sprayed surfaces. The stabilizers and the ingrowth/outgrowth surfaces can be formed of cobalt-chrome alloys or titanium alloys coated with known osteo-conductive materials, such as Hydroxyapatite or Tri-calcium phosphate.

The modular acetabular cup of the invention may be packaged in a kit for convenient use. The kit may include a sterile container that carries one or more extension members and acetabular cups of various configurations and means for securing each other against relative movement as described above. The kit also may include bone cement, as well as mechanical fasteners such as locking screws, bone screws and the like. A wrenching tool for tightening these fasteners also may be included in the kit. The sterile tray containing the acetabular cup, extension member, and other components is placed in an outer envelope and is sealed with a cover to establish a package, all in a manner well known in the packaging of surgical items to be brought into the sterile environment of an operating room.

It will be seen that the present invention provides a modular acetabular cup that can be fitted into bone cavities that have a variety of shapes without the need to have available multiple acetabular cups and also to reduce the sculpturing to a specific shape prior to or during the implant procedure. Use of the modular acetabular cups of the invention thereby simplifies the implant procedure and reduces the time required to implant an acetabular cup device. The modular acetabular cups of the invention also enable development of the most appropriately shaped implant, reduces the need to carry an inventory of differing shaped acetabular cup type implants, and enhances patient safety.

It is to be understood that the above detailed description of the invention is provided by way of example only. Various details of design and construction may be modified without departing from the true spirit and scope of the invention as set forth in the appended claims.

What is claimed is:
1. A prosthetic acetabular cup, comprising:
a first part defining an open hollow interior portion and having an outer surface including a first portion for engaging surface of a bone and a second portion; and
a second part having an inner surface coupled to the second portion of said outer surface of the first part, said second part having an outer surface for engaging the bone wherein the outer surface of the second part and the first portion of the outer surface of the first part together form a substantially non-hemispherical surface adapted to be received in and for engaging the bone within an elongated acetabular cavity; and
wherein said second outer surface portion of the first part defines at least one outwardly projecting member and said inner surface of the second part defines a complimentary shaped recess receiving said projecting member to form means for locking said first and second parts together; and wherein said projecting member comprises a rib extending around said second portion of said first part that mates with a groove defined in said second part and said locking means comprises a threaded element passing through a threaded hole in said second part and received in a recess in the first part.

2. A prosthetic acetabular cup, comprising:
a first part defining an open hollow interior portion and having an outer surface including a first portion for engaging surface of a bone and a second portion; and
a second part having an inner surface coupled to the second portion of said outer surface of the first part, said second part having an outer surface for engaging the bone wherein the outer surface of the second part and the first portion of the outer surface of the first part together form a substantially non-hemispherical surface adapted to be received in and for engaging the bone within an elongated acetabular cavity; and
wherein said second outer surface portion of the first part defines at least one outwardly projecting member and aid inner surface of the second part defines a complimentary shaped recess receiving said projecting member to form means for locking said first and second parts together; and
wherein said projecting member comprises an antirotation key having a square cross-section extending from said first part, received in a square, mating recess in said second part and said locking means further comprises a threaded element passing through said first part and received in a threaded hole in said second part.

3. A prosthetic acetabular cup, comprising:
a first part defining an open hollow interior portion and having an outer surface including a first portion for engaging surface of a bone and a second portion; and
a second part having an inner surface coupled to the second portion of said outer surface of the first part, said second part having an outer surface for engaging the bone wherein the outer surface of the second part and the first portion of the outer surface of the first part together form a substantially non-hemispherical surface adapted to be received in and for engaging the bone within an elongated acetabular cavity; and
wherein said second outer surface portion of the first part defines at least one outwardly projecting member and said inner surface of the second part defines a complimentary shaped recess receiving said projecting member to form means for locking said first and second parts together; and
wherein said projecting member comprises an antirotation key having a square cross-section extending from the first part, received in a square mating recession in the second part, and said locking means further comprises a second, tapered projection extending from the second portion of said first part for engaging a mating tapered recess in said second part.

4. The prosthetic acetabular cup according to claim 1, 2 or 3 wherein said locking means further comprises a layer of a bone cement between the first portion of said first part and said second part.

5. The prosthetic acetabular cup according to claim 1, 2 or 3 wherein the outer surface of the first part is substantially hemispherical and said hollow interior has a substantially hemispherical interior surface, with said outer surface and inner surface formed around a polar axis and terminating at a first part base surface.

6. The prosthetic acetabular cup according to claim 5, wherein said outer surface of the second part terminates at a second part base portion lying in substantially the same plane as the first part base portion.

7. The prosthetic acetabular cup according to claim 6, wherein said substantially non-hemispherical surface formed by the outer surface of the second part and the first portion of the outer surface of the first part is substantially continuous.

8. A kit for forming a modular prosthetic acetabular cup comprising:
at least one first part having an outer surface including a first portion thereof for engaging a surface of a bone and a second portion, and said part defining an open hollow interior portion; and
a plurality of second parts each having an inner surface configured and dimensioned to engage the second portion of the outer surface of said at least one first part, said second part having an outer surface for engaging the bone wherein the outer surface of the first part are configured and dimensioned such that when said parts are engaged, said surfaces together form a substantially non-hemispherical surface adapted to be received in and for engaging the bone within an elongated acetabular cavity; and
wherein said second outer surface portion of the first part defines at least one outwardly projecting member and said inner surfaces of said second parts define complimentarily shaped recesses adapted for receiving said projecting member to form means for locking said first and second parts together; and
wherein said projecting member comprises an antirotation key having a square cross-section extending from said first part configured and dimensioned to be received in a square mating recess in said second parts, said kit further comprising at least one threaded fastener adapted to be received in a threaded hole in said second parts to form a part of said locking means.

9. A kit for forming a modular prosthetic acetabular cup comprising:
at least one first part having an outer surface including a first portion thereof for engaging a surface of a bone and a second portion, and said part defining an open hollow interior portion; and
a plurality of second parts each having an inner surface configured and dimensioned to engage the second portion of the outer surface of said at least one first part, said second part having an outer surface for engaging the bone wherein the outer surface of the first part ar configured and dimensioned such that when said parts are engaged, said surfaces together form a substantially non-hemispherical surface adapted to be received in and for engaging the bone within an elongated acetabular cavity; and
wherein said second outer surface portion of the first part defines at least one outwardly projecting member and said inner surfaces of said second parts define complimentarily shaped recesses adapted for receiving said projecting member to form means for locking said first and second parts together; and wherein said projecting member comprises an anti-rotation key having a square cross-section extending from the first part, said anti-rotation key being configured and dimensioned to be received in a square mating recess in said second parts, and said locking means further comprises a second, tapered projection extending from the second portion of said first part configured and dimensioned to engage a mating tapered recess in said second part.

10. A kit for forming a modular prosthetic acetabular cup comprising:

at least one first part having an outer surface including a first portion thereof for engaging a surface of a bone and a second portion, and said part defining an open hollow interior portion; and a plurality of second parts each having an inner surface configured and dimensioned to engage the second portion of the outer surface of said at least one first part, said second part having an outer surface for engaging the bone wherein the outer surface of the first part are configured and dimensioned such that when said parts are engaged, said surfaces together form a substantially non-hemispherical surface adapted to be received in and for engaging the bone within an elongated acetabular cavity; and wherein said second outer surface portion of the first part defines at least one outwardly projecting member and said inner surfaces of said second parts define complimentarily shaped recesses adapted for receiving said projecting member to form means for locking said first and second parts together; and wherein said projecting member comprises a rib extending around said second portion of said first part configured and dimensioned to mate with a groove defined in said second parts and said kit further comprises a threaded element adapted to pass through a threaded hole in said second part and to be received in a recession in said first part to form a part of said locking means.

11. The kit of claim 10 further comprising a wrenching tool adapted to engage and turn said threaded element.

12. The kit of claim 11 further wherein said first part, said plurality of second parts, said threaded element and said tool are provided in a container.

13. The kit according to claim 8, 9 or 10, wherein the outer surface of the first part is substantially hemispherical and said hollow interior has a substantially hemispherical interior surface, with said outer surface and inner surface formed around a polar axis and terminating at a first part base surface.

14. The kit according to claim 13, wherein said outer surface of the second part terminates at a base portion; and said first and second parts are configured and dimensioned such that when engaged, the respective base portions of said first and second parts lie in substantially the same plane.

15. The kit according to claim 14, wherein said substantially non-hemispherical surface formed by the outer surface of the second part and the first portion of the outer surface of the first part is substantially continuous.

* * * * *